United States Patent [19]

Gauvry

[11] 4,334,528

[45] Jun. 15, 1982

[54] KNEE STRAP

[75] Inventor: George R. Gauvry, Hainesport, N.J.

[73] Assignee: Cho-Pat, Inc., Hainesport, N.J.

[21] Appl. No.: 170,711

[22] Filed: Jul. 21, 1980

[51] Int. Cl.³ ............................................. A41D 13/06
[52] U.S. Cl. .......................................... 128/80 C; 2/24
[58] Field of Search ....................... 128/80 C, 165, 169,
128/75, 78, 76; 2/24

[56] References Cited

U.S. PATENT DOCUMENTS 3,942,525 3/1976 Dragan ................................... 128/165
4,219,892 9/1980 Rigdon ................................. 128/80 C

FOREIGN PATENT DOCUMENTS 794292 2/1936 France ............................... 128/80 C Primary Examiner—Robert Peshock
Attorney, Agent, or Firm—Duffield & Lehrer

[57] ABSTRACT

A knee strap for treating chondromalacia patella and similar disorders includes an elongated soft, flexible strap member which is long enough to encircle a person's leg just below the patella. The ends of the strap are flat and overlap each other behind the person's knee with Velcro holding the ends together. The center portion of the strap includes a rubber, tubular member which presses against the patella tendon to force the patella into proper alignment thereby reducing pressure and trauma on the underside thereof.

4 Claims, 6 Drawing Figures

U.S. Patent  Jun. 15, 1982  4,334,528
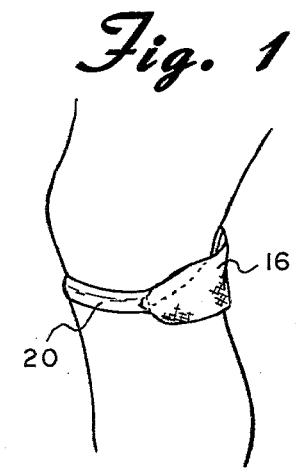
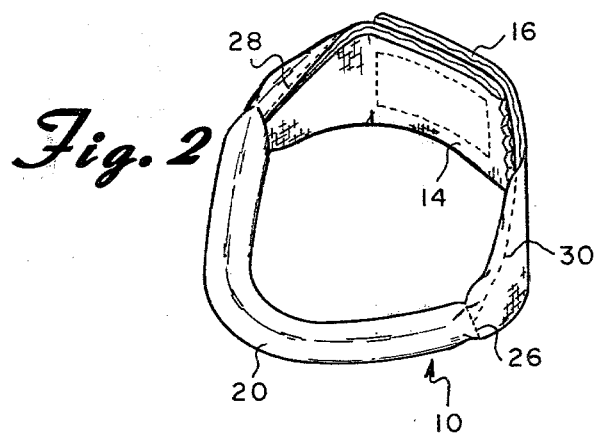
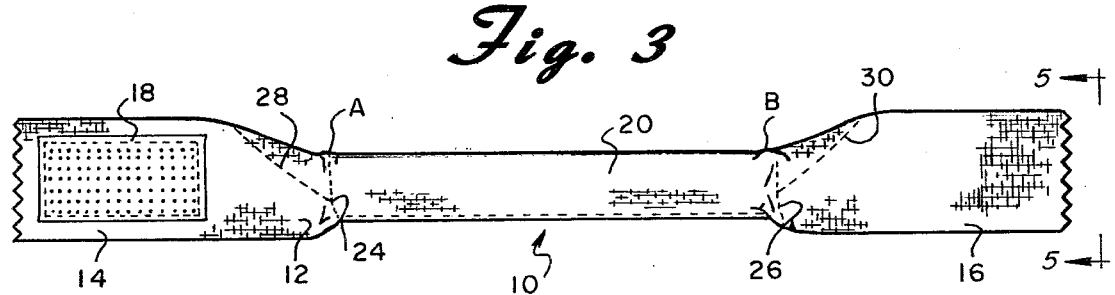
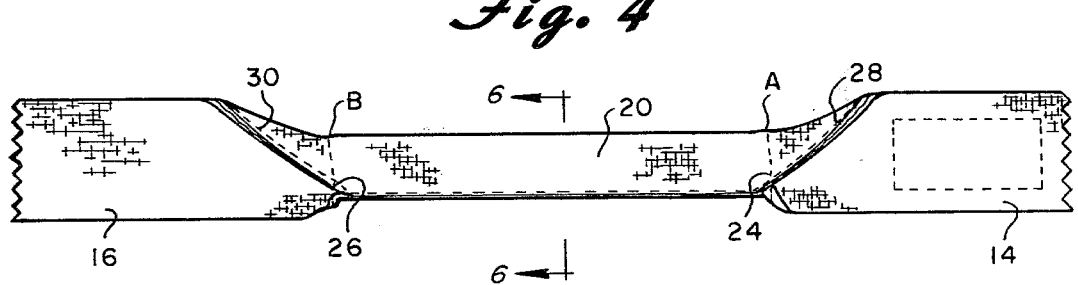
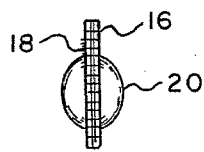
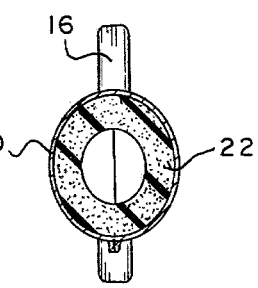

KNEE STRAP

BACKGROUND OF THE INVENTION

The present invention is directed toward a knee strap for treating chondromalacia patella and more particularly toward such a device which is easy to apply and comfortable to wear and which significantly decreases the pain and discomfort suffered by patients with this condition.

It is estimated that approximately one out of every five persons in this country has or will have knee trouble of some kind. The majority of such persons will develop what is commonly called chondromalacia patella. As is known in the art, this term means the softening or degeneration of the undersurface of the patella or kneecap.

Many factors contribute to a person developing chondromalacia patella although the exact mechanism and reason for developing the condition is not truly known. Briefly, if the leg structure is such that the patella is continuously forced outwardly, it will bump against the condyles or bulbous ends of the femur. This causes uneven pressure on the patella. That is, the surface area is less and a given force will be multiplied many times leading to degeneration, inflammation of the synovial lining of the joint, swelling, pain and crepitus on knee motion. Some persons ultimately require surgery to correct this problem.

Another problem with the patello-femoral mechanism is subluxation of the patella. This is the dislocation, usually laterally, of the patella. The patella slips out of the groove formed by the condyles and further traumatizes the undersurface of the patella.

Basically, the solution to the problem of chondromalacia patella and patellar subluxation is to control the patella and force it to stay in proper alignment. Proper alignment keeps the pressures on the underside of the patella reduced by sharing the load over a larger area.

There are knee braces on the market which attempt to solve the foregoing problems. These are basically of two types. Each is a large sleeve-type member which either pulls over the leg or is fastened about the knee with straps or Velcro or the like. The first type of brace has an opening around the patella and includes pads or buttresses laterally, medially or above the patella. The object of this type of brace is to prevent a patella from riding or shifting laterally. The sleeve-type of brace without the opening for the patella attempts to force the patella into the groove of the condyles by compression, thus increasing the surface area under the patella which decreases the pressure area.

These prior art devices suffer from many disadvantages. Among others, it is difficult to keep the braces in place since they have a tendency to creep, ride down or bunch up behind the knee. These devices restrict knee motion due to bunching in back of the knee and they can cause heat rash due to poor evaporation of perspiration. The sleeve-type devices are difficult for older patients to pull on and cannot be loosened if they become uncomfortable in which case the device is usually removed and therefore is of no help. These prior devices also provide poor stabilization of the patella which moves in multiple planes and directions. Even further, the appearance of these prior braces is not particularly pleasing and they are, therefore, not usually worn by persons other than athletes or other sports minded individuals. These relatively expensive prior devices are also normally not available in smaller sizes to fit children who very often have patellar subluxation problems.

SUMMARY OF THE INVENTION

The present invention overcomes the above-described problems of prior art devices and provides an effective and inexpensive device for treating chondromalacia patella and related problems. Rather than controlling the patella, which is relatively mobile, the present invention controls the patella tendon. The knee strap of the present invention includes an elongated soft, flexible strap member which is long enough to encircle a person's leg just below the patella. The ends of the strap are flat and overlap each other behind the person's knee with Velcro holding the ends together. The center portion of the strap includes a rubber, tubular member which presses against the patella tendon to force the patella into proper alignment thereby reducing pressure and trauma on the underside thereof.

BRIEF DESCRIPTION OF THE DRAWING

For the purpose of illustrating the invention, there is shown in the accompanying drawing one form which is presently preferred; it being understood that the invention is not intended to be limited to the precise arrangements and instrumentalities shown.

FIG. 1 is a perspective view of a knee strap constructed in accordance with the principles of the present invention and shown in use on a person's leg;

FIG. 2 is a perspective view of the device shown in FIG. 1 in its closed, encircling condition;

FIG. 3 is a front view of the device shown in FIGS. 1 and 2 in its fully opened position;

FIG. 4 is a view similar to FIG. 3 showing the reverse side thereof;

FIG. 5 is a right end view of the device shown in FIG. 3, and

FIG. 6 is a cross-sectional view taken through the line 6—6 of FIG. 4.

DETAILED DESCRIPTION OF THE PREFERRED EMBODIMENT

Referring now to the drawing in detail wherein like reference numerals have been used throughout the various figures to designate like elements, there is shown in the figures a knee strap constructed in accordance with the principles of the present invention and designated generally as 10. Knee strap 10 is comprised essentially of an elongated strap member 12 having a length of approximately 17 inches. The length of the strap member 12 can, of course, be increased to make larger knee straps for larger persons and can be made somewhat shorter for use by smaller persons. The length of the strap member 12 must be sufficient to encircle the user's leg at a point immediately below the kneecap as shown in FIG. 1.

The strap member 12 includes a pair of end portions 14 and 16 which are substantially flat and substantially flexible. In the preferred embodiment of the invention, the height of the end portions 14 and 16 are approximately 2 inches and have a thickness of approximately ¼ inch. End portion 14 has a pad of Velcro hook material 18 sewn therein as shown most clearly in FIG. 3. Preferably, the entire strap member 12 or at least the end portion 16 is comprised of a cloth-like material such as Tricot or the like which cooperates with the Velcro hooks 18 to fasten the ends 14 and 16 together in the manner shown in FIGS. 1 and 2. That is, the rear surface of the end portion 16 (as viewed in FIG. 3) overlaps and overlies the Velcro hooks 18. This acts as a releasable and adjustable fastening means as is well known to those skilled in the art.

Located between the end portions 14 and 16 is a rounded center portion 20. Center portion 20 is preferably at least one-third the length of the entire strap member 12 so that, when in place, it extends around the front of the leg and just to either side of the patella, as shown most clearly in FIG. 1. As can be seen in FIG. 6, the center portion 20 is preferably comprised of a latex rubber tube 22 which is encircled by the same material which forms the remaining parts of the strap member 12.

Again, in the preferred embodiment of the invention, the latex rubber tube 22 is approximately 6 inches long, has an inner diameter of approximately 3/16 inch and an outer diameter of approximately ⅜ inch so that the overall outer diameter of the center portion 20 is approximately ⅝ inch. Since the center portion 20 incorporates the latex tube 22 therein, the center portion 20 of the strap member 12 is substantially more rigid than the end portions 14 and 16 but is still somewhat flexible.

The knee strap 10 of the present invention is preferably constructed in the following manner. First, a piece of Beta Pile II material (also known as Tricot on ¼ inch foam) is provided which has a length of approximately 17½ inches, a height of 2 inches and a thickness of approximately ¼ inch. The material is laid horizontally and flat on a flat surface and the same is then folded in half along the entire length thereof. The edges are then sewn together along the center 6 inches of the material between the points A and B shown in FIG. 3. This creates a tube of the material having a length of approximately 6 inches.

Into the tube of material thus formed, is inserted the 6-inch long latex rubber tubing. With the latex tube 22 centered within the cloth tube, the cloth tube is stitched closed by stitching 24 and 26 (see FIG. 3). The end portions 14 and 16 are then opened and laid flat on the work surface. The material at the upper half of each end of the tube is then folded to form a taper and is stitched such as shown at 28 and 30 in FIG. 3. The Velcro hook material 18 is then sewn to the unfolded side of the end portion 14 with a border remaining there around.

The knee strap 10 of the present invention is utilized in the following manner. While sitting or standing with the knee straight (extended), the center portion 20 of the strap is placed just below the kneecap. The end portions 14 and 16 are wrapped around the leg behind the knee and are fastened together utilizing the Velcro 18. Necessary adjustments in the tightness are made for a comfortable fit.

With the knee strap 10 in place as shown in FIG. 1, the center portion 20 controls the patella tendon. By applying force on the tendon, the patella is forced into the femoral condyle groove, thus increasing the surface area in contact with the condyles. The force on the underside of the patella is therefore reduced by spreading the same over a larger area as explained above. In addition, the strap tends to lift the patella upward and forces the fat pad beneath the patella slightly under the patella in full extension. Again, the pressure against the condyles is relieved which decreases the trauma and resulting inflammatory reaction mentioned above.

Patients with subluxation patellas will also benefit from the forces on the patella tendon. This dynamic force holds the patella in the groove, dynamically shortening the tendon and thus tightening the whole patellofemoral mechanism. It is also believed that the strap can help relieve patella tendonitis much like an elbow strap relieves tennis elbow. Even further, it is believed that ilio-tibial band friction syndrome can be relieved since the strap appears to act as a checkrein and tends to guide the tendons or cause firm contact to occur between ligaments, tendon and bone.

While specific materials have been described above as preferred materials for manufacturing the present invention, it should be understood that other materials could be substituted therefor. For example, in lieu of the Tricot on foam, natural or man-made leather or the like may be used as well as cotton webbing, elastic webbing, rubber-like sheeting material, canvas or ducking material or the like and various laminated-type materials such as reticulated polyurethane foam sandwiched by nylon, vinyl or similar other materials. Similarly, the latex tube 22 could be made from various other materials such as rolled cotton, felt, foam, leather, etc. This core 22, also, need not necessarily be tubularly shaped but could be solid although it should be preferably somewhat compressible and/or elastic. The Velcro fastening device is the most convenient but could, of course, be replaced by buckles, snaps, friction holders, pressure sensitive materials or various other equivalent fastening means.

The present invention may be embodied in other specific forms without departing from the spirit or essential attributes thereof and accordingly, reference should be made to the appended claims rather than to the foregoing specification as indicating the scope of the invention.

We claim:

1. A knee strap for aiding in the alignment of a patient's patella for reducing trauma on the undersurface of the patella comprising:

an elongated fabric strap member having a length at least as long as the circumference of the patient's leg at a point immediately below the patella so that said strap member can be wrapped there around;

said member including a pair of end portions and a substantially tubularly shaped center portion of circular cross section, said center portion being comprised of part of said fabric wrapped about a compressible tubular member, said end portions extending from either end of said center portion and also being comprised of said fabric;

each of said end portions being substantially flat and substantially flexible;

Velcro fastening means associated with said end portions for fastening the same together when the knee strap is in place on a patient's leg so as to form a closed loop;

said center portion being more rigid than said end portions and having a diameter which is less than the height of said end portions.

2. The knee strap as claimed in claim 1 wherein the length of said center portion is at least one-third of the entire length of said strap member.

3. The knee strap as claimed in claim 1 wherein said center portion has a diameter which is greater than the thickness of said end portions.

4. The knee strap as claimed in claim 1 wherein said center portion is substantially compressible.

* * * * *